United States Patent
Rubin-Wilson et al.

(10) Patent No.: US 7,071,385 B2
(45) Date of Patent: Jul. 4, 2006

(54) PROMOTER AND INTRON FROM MAIZE ACTIN DEPOLYMERIZING FACTOR

(75) Inventors: Beth C. Rubin-Wilson, Indianapolis, IN (US); Kelley A. Smith, Lebanon, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 172 days.

(21) Appl. No.: 10/378,810

(22) Filed: Mar. 4, 2003

(65) Prior Publication Data
US 2003/0213009 A1 Nov. 13, 2003

Related U.S. Application Data

(63) Continuation of application No. 09/718,757, filed on Nov. 22, 2000, now abandoned.

(60) Provisional application No. 60/167,111, filed on Nov. 23, 1999.

(51) Int. Cl.
*A01H 5/00* (2006.01)
*A01H 5/10* (2006.01)
*C12N 15/82* (2006.01)
*C12N 15/11* (2006.01)

(52) U.S. Cl. .................. 800/298; 536/24.1; 435/320.1
(58) Field of Classification Search ............... 536/24.1; 800/298, 278

See application file for complete search history.

(56) References Cited

U.S. PATENT DOCUMENTS 6,673,910 B1* 1/2004 Breton ..................... 536/23.1

OTHER PUBLICATIONS

Maiti et al, 1997, Transgen. Res., 6:143-156.*
Chen et al, 2000, Sex. Plant Reprod. 13:85-94.*
Benfrey et al, 1990, Science 250:959-966.*
Kim et al, 1994, Plant Mol. Biol. 24:105-117.*

* cited by examiner

*Primary Examiner*—Anne Kubelik
(74) *Attorney, Agent, or Firm*—Kenneth B. Ludwig

(57) ABSTRACT

The promoter from the maize actin depolymerizing factor gene is useful in controlling transgene expression in plants.

4 Claims, No Drawings

SEQUENCE LISTING

<160> NUMBER OF SEQ ID NOS: 2

<210> SEQ ID NO 1
<211> LENGTH: 2253

```
<212> TYPE: DNA
<213> ORGANISM: Artificial Sequence
<220> FEATURE:
<223> OTHER INFORMATION: Description of Artificial Sequence:AP2/BC294
      PCR Product

<400> SEQUENCE: 1
cgcccgggca ggtaaatagc aagtgatttt ctctctatgg attccatcta ttttcctggc      60
caccaaacta gccttaagat ttgttttgtc tggatagcac aaaaattgtc catcttgctt     120
gcacccataa cactgccttg aacagaagat gcatgattac ctgcatgcat tgaacgacat     180
accagataag tgccaccagt accacaaact tacatctcgg agacacctta ctatatgatt     240
tatgttgtca caacatacag gtattatact cacttcttag agttgtattt ttatattcgt     300
attgtagtgt aatttgattt gtattagttt agttctgtat tggttgtttc taaaaaaatc     360
gttagattat atcgataata tatgtggtat tcgttttttac gtaatcattg tgcactaaca     420
ttttgttgaa tatattatat accgttgcaa cgcacgggca cccaactagt ctattcatta     480
ttttcccagg atgctcattc cgaaatctct ctcgcggaga agaaaacgaa cgaaagatca     540
cgaaagatcg cgcatcggcg gcccgtccat ctcgacatcc gacgaccgcg caagctcgca     600
gtgggccgct ccgttccgtc gcggggcagc taccgcctac cacacccccg ctccccgcac     660
cgcacggacc gggtggtaa aacccggcga ccacatcaaa acacgaggcg tccccgactc     720
cgcagtccgc aggaccggtc actcggcacg caggctagca gcacagcagc agccagagcc     780
atccctctc ctcgctacgc ttcgcttcct cggcgccgat tcctcctcct cctcctccac     840
cctcgtccgt cccttccgg cgcacgagct cgcccgagat ggtaaggccc ccgctcccat     900
ccgctacccc tccctcccccc tccgcgcact ctggttcctc cccggatcgg cgagcgcgtg     960
ctgattccgg gccttctgtt ctcgcggagc ggtagcgtag cgcttcggat ctagttggat    1020
tcagggggtg aggaggatcg ccgctgctcg gcttgctcgt gggctgattc gtggtttcgt    1080
cgggagggag ttctgatcgg gatcatgggg ttgttcatgg ttccgtgacg cttgggagcc    1140
agaaacttgc gtgggattcc gcgatctgtg gcttggatttt ctggctcttc gtctagcgct    1200
agctgcagac cgtggcgtgg tgcgcggccg cttggatccg ttgctgtttg cgccgtgcgg    1260
tgtaaaatcg aactgtttag atctaagtcc cgctagatgc cgtggcggtg gaatctcggt    1320
tgatctgtgt gtctgagcgc ctgtgtagct cttgtggctg taacatacat ctgctgattt    1380
ggctctcgac ggcttaggcc gcgggagcct agatggcgga gcaccagctg ctccctaatc    1440
aggttggttc tcgtgtggat ctgttgactt gactgtaggt tgcagacttg cagtaggacg    1500
ctggcactgc cattgaccag gagctgcaca acagggcga agctaggtta tttttaggag    1560
gtgcagatag gggtggtaat gacctctaga ttttgcacta taaatgtaa tgatcggatc    1620
gaatcgggat catcctccat tcctattcat ttttgaacta aaaataatta agggccctaa    1680
cttattatga agaaacattt gggtcgtgat ccactactac ccctagggg agatgcaccc    1740
caaaaaaatt ctatagattt agttaaaatt tcaccatata tgcatcccta taaaaaattc    1800
ttatgcacat tcaattttgt tctagcttcg ccactgagta ctgagcacta gcataagaat    1860
tttgttctag aatatgtggc ggtagtatac cctgctagca ctcactaggt gtctcccact    1920
ctcccgagaa atgcgtttct tgtttagaca cttggcacta tcggtcgaga gtcaagacta    1980
tgagctgaac tgctgaaatg tctaatgtta gcagtttctg cactggttca attgcagcct    2040
gatttagaaa tgctggggac agctggctgt gccatgcaaa ataaaatgtg gtagtaggta    2100
cttttgaaggg agactcaaac tttgcatttc caattaacca tgatttaact tgtggttgca    2160
```

```
ggcgaacgcg agatcgggtg tcgctgtgaa cgatgagtgc atgctgaagt ttggcgagct    2220
gcagtcgaag aggctgcacc gcttcataac ttt                                 2253

<210> SEQ ID NO 2
<211> LENGTH: 5796
<212> TYPE: DNA
<213> ORGANISM: Artificial Sequence
<220> FEATURE:
<223> OTHER INFORMATION: Description of Artificial Sequence:pDAB305

<400> SEQUENCE: 2
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cccgatctag taacatagat    420
gacaccgcgc gcgataattt atcctagttt gcgcgctata ttttgttttc tatcgcgtat    480
taaatgtata attgcgggac tctaatcata aaaacccatc tcataaataa cgtcatgcat    540
tacatgttaa ttattacatg cttaacgtaa ttcaacagaa attatatgat aatcatcgca    600
agaccggcaa caggattcaa tcttaagaaa ctttattgcc aaatgtttga acgatcgggg    660
aaattcgagc tctccaattc cccaccgagg ctgtagccga cgatggtgcg ccaggagagt    720
tgttgattca ttgtttgcct ccctgctgcg ttttttcacc gaagttcatg ccagtccagc    780 gttttttgcag cagaaaagcc gccgacttcg gtttgcggtc gcgagtgaag atcccttttct   840 tgttaccgcc aacgcgcaat atgccttgcg aggtcgcaaa atcggcgaaa ttccatacct    900
gttcaccgac gacggcgctg acgcgatcaa agacgcggtg atacatatcc agccatgcac    960
actgatactc ttcactccac atgtcggtgt acattgagtg cagcccggct aacgtatcca   1020
cgccgtattc ggtgatgata atcggctgat gcagtttctc ctgccaggcc agaagttctt   1080
tttccagtac cttctctgcc gtttccaaat cgccgctttg gacataccat ccgtaataac   1140
ggttcaggca cagcacatca aagagatcgc tgatggtatc ggtgtgagcg tcgcagaaca   1200
ttacattgac gcaggtgatc ggacgcgtcg ggtcgagttt acgcgttgct ccgccagtg    1260 gcgaaatatt cccgtgcact tgcggacggg tatccggttc gttggcaata ctccacatca   1320
ccacgcttgg gtggttttg tcacgcgcta tcagctcttt aatcgcctgt aagtgcgctt   1380
gctgagtttc cccgttgact gcctcttcgc tgtacagttc tttcggcttg ttgcccgctt   1440
cgaaaccaat gcctaaagag aggttaaagc cgacagcagc agtttcatca atcaccacga   1500
tgccatgttc atctgcccag tcgagcatct cttcagcgta agggtaatgc gaggtacggt   1560
aggagttggc cccaatccag tccattaatg cgtggtcgtg caccatcagc acgttatcga   1620
atcctttgcc acgtaagtcc gcatcttcat gacgaccaaa gccagtaaag tagaacggtt   1680
tgtggttaat caggaactgt tcgcccttca ctgccactga ccggatgccg acgcgaagcg   1740
ggtagatatc acactctgtc tggcttttgg ctgtgacgca cagttcatag agataacctt   1800
cacccggttg ccagaggtgc ggattcacca cttgcaaagt cccgctagtg ccttgtccag   1860
ttgcaaccac ctgttgatcc gcatcacgca gttcaacgct gacatcacca ttggccacca   1920
```

-continued

```
cctgccagtc aacagacgcg tggttacagt cttgcgcgac atgcgtcacc acggtgatat    1980
cgtccaccca ggtgttcggc gtggtgtaga gcattacgct gcgatggatt ccggcatagt    2040
taaagaaatc atggaagtaa gactgctttt tcttgccgtt ttcgtcggta atcaccattc    2100
ccggcgggat agtctgccag ttcagttcgt tgttcacaca aacggtgata cgtacacttt    2160
tcccggcaat aacatacggc gtgacatcgg cttcaaatgg cgtatagccg ccctgatgct    2220
ccatcacttc ctgattattg acccacactt tgccgtaatg agtgaccgca tcgaaacgca    2280
gcacgatacg ctggcctgcc aaccttttcg gtataaagac ttcgcgctga taccagacgt    2340
tgcccgcata attacgaata tctgcatcgg cgaactgatc gttaaaactg cctggcacag    2400
caattgcccg gctttcttgt aacgcgcttt cccaccaacg ctgatcaatt ccacagtttt    2460
cgcgatccag actgaatgcc acaggccgt cgagtttttt gatttcacgg ttgggtttt     2520
ctacaggacg gaccatggct gaatgcttat cccgtgcctg gaacaaatgg ccccagatcc    2580
gtccgcagct gcacgggtcc aggaaagcaa tcgcatagtc aagctaaatc atcaagatgc    2640
aaacttttcg cccttgctaa acacggtaaa attcgaatgg acatgtgtgg agcagcaaag    2700
gagctttccc caaaattact caacgaatca taaaccaaga ttagtcagat caagagacag    2760
aggagaaaca aggcggacct ttgcacttga tctggggatt gccctgactt ggtggtgctg    2820
gtatattagg gatagggttg ctcctatcca cagcttgtcc accaaatatc agctcctccg    2880
tggactgcct tgtcgagcct tcagctggat cctctagagt ccccgtgttt ctctccaaat    2940
gaaatgaact tccttatata gaggaagggg cttgcgaagg atagtgggat tgtgcgtcat    3000
cccttacgtc agtggagata tcacatcaat ccacttgctt tgaagacgtg gttggaacgt    3060
cttctttttc cacgatgctc ctcgtgggtg ggggtccatc tttgggacca ctgtcggcag    3120
aggcatcttc aacgatggcc tttcctttat cgcaatgatg gcatttgtag gagccacctt    3180
cctttttccac tatcttcaca ataaagtgac agatagctgg gcaatggaat ccgaggaggt    3240
ttccggatat tacccttgt tgaaaagtct ccatcgatga tcacatcaat ccacttgctt     3300
tgaagacgtg gttggaacgt cttctttttc cacgatgctc ctcgtgggtg ggggtccatc    3360
tttgggacca ctgtcggcag aggcatcttc aacgatggcc tttcctttat cgcaatgatg    3420
gcatttgtag gagccacctt cctttttccac tatcttcaca ataaagtgac agatagctgg    3480
gcaatggaat ccgaggaggt ttccggatat tacccttgt tgaaaagtct ccacccatgc     3540
agatctgcag gcatgcaagc ttggcgtaat catggtcata gctgtttcct gtgtgaaatt    3600
gttatccgct cacaattcca cacaacatac gagccggaag cataaagtgt aaagcctggg    3660
gtgcctaatg agtgagctaa ctcacattaa ttgcgttgcg ctcactgccc gctttccagt    3720
cgggaaacct gtcgtgccag ctgcattaat gaatcggcca acgcgcgggg agaggcggtt    3780
tgcgtattgg gcgctcttcc gcttcctcgc tcactgactc gctgcgctcg gtcgttcggc    3840
tgcggcgagc ggtatcagct cactcaaagg cggtaatacg ttatccaca gaatcagggg     3900
ataacgcagg aaagaacatg tgagcaaaag gccagcaaaa ggccaggaac cgtaaaaagg    3960
ccgcgttgct ggcgtttttc cataggctcc gcccccctga cgagcatcac aaaaatcgac    4020
gctcaagtca gaggtggcga aacccgacag gactataaag ataccaggcg tttccccctg    4080
gaagctccct cgtgcgctct cctgttccga ccctgccgct taccggatac ctgtccgcct    4140
ttctcccttc gggaagcgtg cgctttctc aatgctcacg ctgtaggtat ctcagttcgg    4200
tgtaggtcgt tcgctccaag ctgggctgtg tgcacgaacc cccgttcag cccgaccgct    4260
gcgccttatc cggtaactat cgtcttgagt ccaacccggt aagacacgac ttatcgccac    4320
```

```
tggcagcagc cactggtaac aggattagca gagcgaggta tgtaggcggt gctacagagt    4380
tcttgaagtg gtggcctaac tacggctaca ctagaaggac agtatttggt atctgcgctc    4440
tgctgaagcc agttaccttc ggaaaaagag ttggtagctc ttgatccggc aaacaaacca    4500
ccgctggtag cggtggtttt tttgtttgca agcagcagat tacgcgcaga aaaaaggat     4560
ctcaagaaga tcctttgatc ttttctacgg ggtctgacgc tcagtggaac gaaaactcac    4620
gttaagggat tttggtcatg agattatcaa aaggatctt cacctagatc cttttaaatt     4680
aaaaatgaag ttttaaatca atctaaagta tatatgagta aacttggtct gacagttacc    4740
aatgcttaat cagtgaggca cctatctcag cgatctgtct atttcgttca tccatagttg    4800
cctgactccc cgtcgtgtag ataactacga tacgggaggg cttaccatct ggccccagtg    4860
ctgcaatgat accgcgagac ccacgctcac cggctccaga tttatcagca ataaaccagc    4920
cagccggaag ggccgagcgc agaagtggtc ctgcaactt  atccgcctcc atccagtcta    4980
ttaattgttg ccgggaagct agagtaagta gttcgccagt taatagtttg cgcaacgttg    5040
ttgccattgc tacaggcatc gtggtgtcac gctcgtcgtt tggtatggct tcattcagct    5100
ccggttccca acgatcaagg cgagttacat gatcccccat gttgtgcaaa aaagcggtta    5160
gctccttcgg tcctccgatc gttgtcagaa gtaagttggc cgcagtgtta tcactcatgg    5220
ttatggcagc actgcataat tctcttactg tcatgccatc cgtaagatgc ttttctgtga    5280
ctggtgagta ctcaaccaag tcattctgag aatagtgtat gcggcgaccg agttgctctt    5340
gcccggcgtc aatacgggat aataccgcgc cacatagcag aactttaaaa gtgctcatca    5400
ttggaaaacg ttcttcgggg cgaaaactct caaggatctt accgctgttg agatccagtt    5460
cgatgtaacc cactcgtgca cccaactgat cttcagcatc ttttactttc accagcgttt    5520
ctgggtgagc aaaaacagga aggcaaaatg ccgcaaaaaa gggaataagg gcgacacgga    5580
aatgttgaat actcatactc ttcctttttc aatattattg aagcatttat cagggttatt    5640
gtctcatgag cggatacata tttgaatgta tttagaaaaa taaacaaata ggggttccgc    5700
gcacatttcc ccgaaaagtg ccacctgacg tctaagaaac cattattatc atgacattaa    5760
cctataaaaa taggcgtatc acgaggccct ttcgtc                              5796
```

PROMOTER AND INTRON FROM MAIZE ACTIN DEPOLYMERIZING FACTOR

This application is a continuation of U.S. application Ser. No. 09/718,757, filed 22 Nov. 2000, now abandoned which claims the benefit of U.S. Provisional Application Ser. No. 60/167,111, filed 23 Nov. 1999.

FIELD OF THE INVENTION

This invention relates to genetic engineering of plants. The invention provides DNA sequences and constructs that are useful to control expression of recombinant genes in plants. More particularly, the invention provides novel regulatory sequences derived from maize actin depolymerizing factor (ADF).

BACKGROUND OF THE INVENTION

Plant genetic engineering projects require access to a variety of genetic elements that are used to regulate transgene expression. Two examples of such genetic elements are promoters and introns.

Initiation of transcription is regulated by a promoter. A given project typically requires use of several different promoters. One promoter will be used to drive the gene of interest, and a different one used, for example, to drive the selectable marker.

A eukaryotic gene is usually interrupted by noncoding sequences called introns. The initial product of transcription of a eukaryotic gene is pre mRNA, which includes sequences corresponding to the introns. The introns are removed during post-transcription processing to provide the mRNA that is translated to produce a protein. Studies characterizing the role of introns in the regulation of gene expression have shown that the first intron of the maize alcohol dehydrogenase gene (Adh-1) has the ability to increase expression under anaerobiosis. Callis J., M. Fromm, and V. Walbot. (1987), Gene Dev. 1:1183–1200. The intron also stimulates expression (to a lesser degree) in the absence of anaerobiosis. This enhancement is thought to be a result of a stabilization of the pre-mRNA in the nucleus. Mascarenhas et al. reported a 12-fold and 20-fold enhancement of CAT expression by use of the Adh-1 intron. Mascarenhas et al., "Intron-Mediated Enhancement of Heterologous Gene Expression in Maize," Plant Molecular Biology, 15:913–920, 1990. Several other introns have been identified from maize and other monocots which increase gene expression. Vain, P. et al. (1996), Plant Cell Reports 15:489–494. See also WO98/5921.

The cDNA sequence for maize ADF is known (GenBank accession no. X97726), but the genomic ADF sequence has not been published. In particular, the sequence for the ADF promoter has not heretofore been published, nor have any ADF introns been identified.

BRIEF DESCRIPTION OF THE SEQUENCES

SEQ ID NO:1 is the DNA sequence for the AP2/BC294 PCR product, including the sequence for the ADF promoter and ADF intron 1.

SEQ ID NO:2 is the DNA sequence for pDAB305.

SUMMARY OF THE INVENTION

The invention provides DNA molecules corresponding to or derived from the ADF promoter and ADF intron 1.

In another of its aspects, the invention provides a DNA construct comprising, operatively linked in the 5' to 3' direction, a) a maize ADF promoter;
b) an untranslated leader sequence
c) an intron;
d) a gene of interest; and
e) a 3' UTR.

In a preferred embodiment the ADF promoter comprises bp 1–734 of SEQ ID NO 1, and the intron is selected from the group consisting of Adh1 intron 1 and ADF intron 1 (bp 882–2161 of SEQ ID NO 1).

In another of its aspects, the invention provides a DNA construct comprising, in the 5' to 3' direction, a) a promoter functional in plants;
b) an untranslated leader sequence;
c) ADF intron 1;
d) a cloning site;
e) a 3' UTR.

In another of its aspects, the invention provides a plasmid comprising a maize ADF promoter, preferably bp 1–878 of SEQ ID NO 1, or the maize ADF intron 1 sequence, preferably bp 882–2161 of SEQ ID NO:1.

In another of its aspects, the invention provides a transformed plant comprising at least one plant cell that contains a DNA construct of the invention. The plant may be a monocot or dicot. Preferred plants are maize, rice, cotton and tobacco.

In another of its aspects, the invention provides seed or grain that contains a DNA construct of the invention.

In one of its aspects, the invention is regarded as encompassing any deleted version of the ADF promoter that provides a functional plant promoter. Such promoters are encompassed by the term "ADF promoter". A sequence will be regarded as providing a "functional" promoter for purposes of this application if the sequence can be substituted for bp 3056–3790 of pDAB 621 or bp 3962–4694 of pDAB625 to produce a construct that gives transient GUS expression above background levels when tested as in Example 5. Those skilled in the art will understand that various deletions from the 733 bp sequence identified as the ADF promoter in SEQ ID NO:1 can be made without destroying functionality of the sequence as a promoter. Deletion experiments are within the skill in the art. Preferably, an ADF promoter of the invention will comprise 200 contiguous base pairs that are identical to 200 contiguous base pairs of the sequence defined by bp 1–734 of SEQ ID NO:1. More preferable are ADF promoters that comprise 500 contiguous base pairs that are identical to 500 contiguous base pairs of the sequence defined by bp 1–734 of SEQ ID NO:1.

Similarly, the invention covers deleted versions of the ADF intron that function to enhance expression when used with a promoter. The term "ADF intron 1" is intended to encompass such deleted versions. Preferably, an ADF intron 1 of the invention will comprise 600 contiguous base pairs that are identical to 600 contiguous base pairs of the sequence defined by bp 882–2161 of SEQ ID NO:1. More preferable are ADF introns that comprise 1000 contiguous base pairs of the sequence defined by bp 882–2161 of SEQ ID NO:1.

DETAILED DESCRIPTION OF THE INVENTION

The ADF promoter is preferably used in constructs having an intron incorporated into the untranslated leader 5' of the gene of interest and 3' of the promoter. Suitable introns include the ADF intron 1, Adh1 intron 1, Ubiquitin intron 1, and Bronze 2 intron 1.

The non-translated leader sequence used in constructs of the invention can be derived from any suitable source and may be specifically modified to increase the translation of the mRNA. The 5' non-translated region may be obtained from the native leader sequence of the promoter, the native leader sequence of the gene or coding region to be expressed, viral RNAs, suitable eukaryotic genes, or may be a synthetic sequence.

The gene of interest used in constructs of the invention may be any gene that it is desired to express in plants. Particularly useful genes are those that confer tolerance to herbicides, insects, or viruses, and genes that provide improved nutritional value or processing characteristics of the plant. Examples of suitable agronomically useful genes include the insecticidal gene from *Bacillus thuringiensis* for conferring insect resistance and the 5'-enolpyruvyl-3'-phosphoshikimate synthase (EPSPS) gene and any variant thereof for conferring tolerance to glyphosate herbicides. As is readily understood by those skilled in the art, any agronomically important gene conferring a desired trait can be used.

The 3' UTR, or 3' untranslated region, employed in constructs of the invention is one that confers efficient processing of the mRNA, maintains stability of the message and directs the addition of adenosine ribonucleotides to the 3' end of the transcribed mRNA sequence. The 3' UTR may be native with the promoter region, native with the structural gene, or may be derived from another source. A wide variety of termination regions are available that may be obtained from genes capable of expression in plant hosts, e.g., bacterial, opine, viral, and plant genes. Suitable 3' UTRs include but are, not limited to: the per5 3' UTR (WO98/56921), the 3' UTR of the nopaline synthase (nos) gene, tmL 3', or acp 3', for example.

The present invention is generally applicable to the expression of structural genes in both monocotyledonous and dicotyledonous plants. This invention is particularly suitable for any member of the monocotyledonous (monocot) plant family including, but not limited to, maize, rice, barley, oats, wheat, sorghum, rye, sugarcane, pineapple, yams, onion, banana, coconut, and dates. A preferred application of the invention is in production of transgenic maize plants. The invention is particularly applicable to the family Graminaceae, in particular to maize, wheat, rice, oat, barley and sorghum. Dicotyledonous species include tobacco, tomato, sunflower, cotton, sugarbeet, potato, lettuce, melon, soybean and canola (rapeseed).

ADF intron 1 can be used with promoters other than the ADF promoter to enhance expression. The promoter used with ADF intron 1 can be any promoter suitable for use in plants. The promoter selected should be capable of causing sufficient expression of the desired protein alone, but especially when used with ADF intron 1, to result in the production of an effective amount of the desired protein to cause the plant cells and plants regenerated therefrom to exhibit the properties which are phenotypically caused by the expressed protein. Suitable promoters can be obtained from a variety of sources, such as plants or plant DNA viruses. Preferred promoters are the ADF promoter, per5 promoter, the 35T promoter (described hereinafter in Examples 20 and 23), and the ubiquitin promoter. Useful promoters include those isolated from the caulimovirus group, such as the cauliflower mosaic virus 19S and 35S (CaMV19S and CaMV35S) transcript promoters. Other useful promoters include the enhanced CaMV35S promoter (eCaMV35S) as described by Kat et al. (1987) *Science* 236:1299–1302 and the small subunit promoter of ribulose 1,5-bisphosphate carboxylase oxygenase (RUBISCO). Examples of other suitable promoters are rice actin promoter; cyclophilin promoter; ubiquitin promoter; ADH1 promoter, Callis et al., supra.; Class I patatin promoter, Bevan et al. (1986) *Nucleic Acids Res.* 14 (11), 4675–4638; ADP glucose pyrophosphorylase promoter; beta.-conglycinin promoter, Tiemey et al. (1987) *Planta* 172: 356–363; E8 promoter, Deikman et al. (1988) *Embo J.* 7 (11) 3315–3320; 2AII promoter, Pear et al. (1989) *Plant Mol. Biol.* 13: 639–651; acid chitinase promoter, Samac et al. (1990) *Plant Physiol.* 93: 907–914;

Construction of a gene cassette utilizing the ADF promoter or ADF intron 1 is readily accomplished utilizing well known methods, such as those disclosed in Sambrook et al. (1989), *Molecular Cloning: A Laboratory Manual*, 2nd edition, Cold Spring; and Ausubel et al. (1987) *Current Protocols in Molecular Biology*, John Wiley and Sons, New York, N.Y. DNA encoding the ADF promoter may be prepared from chromosomal DNA or DNA of synthetic origin by using well-known techniques. Genomic DNA may be isolated by standard techniques. Sambrook et al. (1989); Mullis et al. (1987), *Meth. Enz.*, 155:335. Horton et al. (1989), *Gene,* 77:61.; Erlich (ed.)(1989)). *PCR Technology: Principles and Applications for DNA Amplification*. It is also possible to prepare synthetic sequences by oligonucleotide synthesis. See Caruthers (1983) in: *Methodology of DNA and RNA,* (ed.) Weissman, and Beaucage et al. (1981), *Tetrahedron Letters,* 22:1859–1962).

The present invention-also includes DNA sequences having substantial sequence homology with the specifically disclosed regulatory sequences, such that they are able to have the disclosed effect on expression.

As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. Sequences that have substantial sequence homology with the sequences disclosed herein are usually variants of the disclosed sequence, such as mutations, but may also be synthetic sequences.

In most cases, sequences having 95% homology to the sequences specifically disclosed herein will function as equivalents, and in many cases considerably less homology, for example 75% or 80%, will be acceptable. Locating the parts of these sequences that are not critical may be time consuming, but is routine and well within the skill in the art.

It is contemplated that sequences corresponding to the above noted sequences may contain one or more modifications in the sequences from the wild-type but will still render the respective elements comparable with respect to the teachings of this invention. For example, as noted above, fragments may be used. One may incorporate modifications into the isolated sequences including the addition, deletion, or nonconservative substitution of a limited number of various nucleotides or the conservative substitution of many nucleotides. Further, the construction of such DNA molecules can employ sources which have been shown to confer enhancement of expression of heterologous genes placed under their regulatory control. Exemplary techniques for modifying oligonucleotide sequences include using polynucleotide-mediated, site-directed mutagenesis. See Zoller et al. (1984), DNA, 3:479; Higuchi et al. (1988), Nucl. Acids Res., 16:7351–7367; Horton et al. (1989), Gene, 77:61; and PCR Technology: Principles and Applications for DNA Amplification, (ed.) Erlich (1989).

Conventional technologies for introducing biological material into host cells include electroporation (see Shigekawa and Dower (1988), Biotechniques, 6:742; Miller, et al. (1988), Proc. Natl. Acad. Sci. USA, 85:856–860; and Powell, et al (1988), Appl. Environ. Microbiol., 54:655–660); direct DNA uptake mechanisms (see Mandel and Higa (1972), J. Mol. Biol., 53:159–162; Dityatkin, et al. (1972), Biochimica et Biophysica Acta, 281:319–323; Wigler, et al. (1979), Cell, 16:77; and Uchimiya, et al. (1982), In: Proc. 5th Intl. Cong. Plant Tissue and Cell Culture, A. Fujiwara (ed.), Jap. Assoc. for Plant Tissue Culture, Tokyo, pp. 507–508); fusion mechanisms (see Uchidaz, et al. (1980), In: Introduction of Macromolecules Into Viable Mammalian Cells, Baserga et al. (eds.) Wistar Symposium Series, 1:169–185); infectious agents (see Fraley, et al. (1986), CRC Crit. Rev. Plant Sci., 4:1–46); and Anderson (1984), Science, 226:401–409); microinjection mechanisms (see Crossway, et al. (1986), Mol. Gen. Genet., 202:179–185); and high velocity projectile mechanisms (see EPO 0 405 696 to Miller, Schuchardt, Skokut and Gould, (The Dow Chemical Company)

The appropriate procedure to transform a selected host cell may be chosen in accordance with the host cell used. Based on the experience to date, there appears to be little difference in the expression of genes, once inserted into cells, attributable to the method of transformation itself. Once introduced into the plant tissue, the expression of the structural gene may be assayed in a transient expression system, or it may be determined after selection for stable integration within the plant genome.

Techniques are known for the in vitro culture of plant tissue, and in a number of cases, for regeneration into whole plants. The appropriate procedure to produce mature transgenic plants may be chosen in accordance with the plant species used. Regeneration varies from species to species of plants. Efficient regeneration will depend upon the medium, on the genotype and on the history of the culture. Once whole plants have been obtained, they can be sexually or clonally reproduced in such a manner that at least one copy of the sequence is present in the cells of the progeny of the reproduction. Seed from the regenerated plants can be collected for future use, and plants grown from this seed. Procedures for transferring the introduced gene from the originally transformed plant into commercially useful cultivars are known to those skilled in the art.

In the following examples all molecular biology manipulations were done according to procedures described in Molecular Cloning: A Laboratory Manual (Maniatis, T., Fritsch, E. F., Sambrook, J., 1982, Cold Spring Harbor Laboratory).

EXAMPLE 1

ADF 5' Flanking Sequence

Actin depolymerizing factor gene (Zmbap3) 5' flanking sequences were isolated from maize genomic DNA, var. OQ414 (Dow AgroSciences proprietary line). DNA sequencing was accomplished using the ABI Prism DNA Sequencing Kit with AmpliTaq® Polymerase FS as described by the manufacturer (Perkin Elmer/Applied Biosystems Division, Foster City, Calif.). Sequencing reactions were run on an Applied Biosystem 373A DNA sequencer (Perkin Elmer/Applied Biosystems Division).

The ADF 5' flanking sequence was compared to the published cDNA sequence and found to diverge due to the presence of an intron immediately 3' to the ATG start codon.

The following table indexes the features of the AP2/BC294 PCR product (SEQ ID NO:1):

| FEATURES OF AP2/BC294 PCR PRODUCT | |
|---|---|
| bp of SEQ ID NO: 1 | feature |
| 1–734 | ADF promoter. |
| 735–878 | 5' untranslated leader (agrees with published cDNA sequence) |
| 879–881 | ATG start site |
| 882–2161 | ADF intron |
| 2162–2273 | beginning of ADF coding sequence, (agrees with published cDNA sequence) |

The first two and last two bases of the intron are consensus intron splice site sequences internal to the intron. The sequences just outside of the intron are also nearly consensus.

In the following examples, the ADF promoter and ADF intron were evaluated using expression vectors based on plasmid pDAB305. pDAB305 is a 5796 bp plasmid that harbors a promoter containing tandem copy of the Cauliflower Mosaic Virus 35S enhancer (35S), a deleted version of the Adh1 intron 1, and the untranslated leader from the Maize Streak Mosaic Virus Coat Protein fused to the uidA gene, which is then followed by the nos 3' UTR. The sequence for pDAB305 is given in SEQ ID NO:2. The features of the sequence are described in the following table

| Features of pDAB 305 | |
|---|---|
| bp of SEQ ID NO: 2 | Description of feature |
| 1–401 | correspond to bp 1–401 of pUC19 |
| 404–656 | reverse compliment of nos 3' UTR |
| 657–675 | linker including ScaI restriction site |
| 676–2536 | reverse compliment of bp 26–1889 of Genbank Accession Number U02456, including reverse compliment (bp 728–2536) of uidA gene encoding GUS |
| 2534–2573 | reverse compliment of bases 278–317 of Maize Streak Virus genome. (MSV, Genbank Accession Number X01633 K02026) as given in Mullineaux, P. M., J. Donson, B. A. M. Morris-Krsinich, M. I. Boulton, and J. W. Davies (1984) The nucleotide sequence of Maize Streak Virus DNA. EMBO J. 3: 3063–3068. |
| 2584–2701 | reverse complement of bases 1657–1774 of the maize Adh1S intron 1, deposited as GenBank MZEADH1.S, Accession Number X00581, [Dennis, E. S., W. L. |

-continued

Features of pDAB 305

| bp of SEQ ID NO: 2 | Description of feature |
|---|---|
| | Gerlach, A. J. Pryor, J. L. Bennetzen, A. Inglis, D. Llewellyn, M. M. Sachs, R. J. Ferl, and W. J. Peacock (1984) Molecular analysis of the alcohol dehydrogenase (Adh1) gene of maize. Nucl. Acids Res. 12: 3983–4000]. |
| 2702–2793 | reverse complement of nucleotides 1222–1312 of Adh1S intron 1 of GenBank Acession Number X00581, [bases 119 to 209 of Dennis et al., (ibid.)]. |
| 2795–2904 | reverse complement of nucleotides 167 to 277 of the MSV genome [Genbank Accession Number X01633 K02026, and Mullineaux et al. (ibid.)], except the wild type sequence has an additional T inserted between bases 2884 and 2885 of pDAB305. |
| 2905–2924 | linker including BamHI and XbaI restriction sites |
| 2925–3271 | reverse complement of nucleotides 7093 to 7439 of the Cauliflower Mosaic Virus qenome 35S promoter. (CabbB-S strain, GenBank Accession Number V00141 J02048). |
| 3272–3279 | linker including ClaI site |
| 3280–3531 | reverse complement of nucleotides 7093 to 7344 of GenBank Accession Number V00141 J02048 |
| 3532–3544 | linker |
| 3545–5796 | correspond to bases 435–2686 of pUC19 |

EXAMPLE 2

Construction of pDAB620

Plasmid pDAB620 is essentially pDAB305, but with the ADF promoter replacing the CaMV 35S double enhanced promoter and ADH intron I/MSV intron leader. For cloning the ADF promoter without an intron behind the GUS coding region, the ADF promoter was amplified with primers designed to add a 5' HindIII site and a 3' NcoI site. PCR amplications were performed using 70 ng of template DNA (SEQ ID NO:1 cloned into the PCR®2.1-Topo vector), GeneAmp® 10×PCR Buffer (Perkin Elmer/Applied Biosystems Division), 50 picomoles each primer, and 5 units of AmpliTaq Gold™ polymerase (Perkin Elmer/Applied Biosystems Division) in a total volume of 100 ul. Amplifications were performed using the GeneAmp® PCR System 9600 (PE/ABI) using the following cycle conditions: 96° C. 10 minutes, 94° C., 1 minute, 550 C 2 minutes, 72° C. 3 minutes, 20 cycles, followed-by a 72° C. extension for 7 minutes. The resulting 906 bp PCR product was cloned into the PCR®2.1-Topo (Invitrogen). Individual colonies were selected for DNA extraction and sequencing as described above. For cloning the ADF promoter into pDAB305, the ADF promoter fragment was isolated from the recombinant PCR®2.1-Topo (Invitrogen) clones as a HindIII and NcoI fragment by digestion with NcoI and HindIII restriction enzymes (New England Biolabs, Inc., Beverly, Mass.). The ADF fragment was purified on a preparative agarose gel and the DNA was extracted using GenElute Agarose Spin Columns (Supelco, Inc., Bellefonte, Pa.). Plasmid pDAB305 was prepared by digestion with HindIII and NcoI (New England Biolabs) to drop out the existing promoter and intron. The digested plasmid was run on a preparative agarose gel (FMC), the fragment was cut from the gel, and DNA-extracted from the agarose using GenElute Agarose Spin Columns (Supelco, Inc.). The ADF HindIII/NcoI promoter fragment was combined with the deleted pDAB305 vector and ligated using the Rapid DNA Ligation Kit (Roche Diagnostics formerly Boehringer Mannheim, Indianapolis, Ind.) according to manufacturers instructions. Subcloning Efficiency DH5α™ Competent Cells (Gibco/BRL, Gaithersburg, Md.) were transformed with the ligation mixture according to the protocol included with the cells, and plated on LB media containing 75 ug/ml ampicillin. Plates were incubated overnight at 37° C. Individual colonies were selected for DNA extraction and DNA sequencing as described. Those plasmids which contained the ADF promoter fragment replacing the CaMV promoter/ADH intron I/MSV leader fragment were named pDAB620.

Features of pDAB 620

| bp of pDAB 620 | Description of feature |
|---|---|
| 1–2538 | correspond to bp 1–2538 of pDAB 305 (SEQ ID NO: 2) |
| 2539–2682 | reverse compliment of untranslated leader sequence (bp 735–878 of SEQ ID NO: 1) |
| 2683–3416 | reverse compliment of ADF promoter (bp 1–734 of SEQ ID NO: 1) |
| 3417–5656 | correspond to 3557–5796 of pDAB 305 (SEQ ID NO: 2) |

EXAMPLE 3

Construction of pDAB621

Plasmid pDAB621 differs from pDAB620 of Example 2 in that it contains the ADH/MSV intron leader immediately 3' to the ADF promoter. For cloning the ADF promoter in front of the modified ADH intron I/MSV leader, primers were designed to incorporate a HindIII site and a BamHI site onto the 5' and 3' end of the ADF promoter, respectively, using PCR amplification. PCR amplification of the ADF promoter was performed using a Robocycler® Gradient 96 Temperature Cycler (Stratagene) using the following conditions: 70 ng DNA (SEQ ID NO:1) cloned into PCR®2.1-Topo vector), 15 ul 3.3×XL Buffer II from the GeneAmp® XL PCR kit (Perkin Elmer/Applied Biosystems Division), 50 picomoles each primer, 1 mM magnesium acetate, 0.2 mM each dNTP, 1.5 ul rTth DNA polymerase (Perkin Elmer/Applied Biosystems Division). The product was cloned into the PCR® 2.1 Topo (Invitrogen). Individual colonies were selected and DNA was extracted using a alkaline lysis method. The ADF fragment was purified on a preparative agarose gel and the DNA was extracted using using GenElute Agarose Spin Columns (Supelco, Inc.). For cloning the ADF promoter into pDAB305, the ADF promoter was isolated from the recombinant PCR® 2.1-Topo (Invitrogen) clones as a HindIII and BamHI fragment. Plasmid pDAB305 was prepared by digestion with HindIII and BamHI (NEB) to drop out the existing promoter. The ADF HindIII/BamHI promoter fragment was combined with the deleted pDAB305 and ligated using the Rapid DNA Ligation Kit (Roche Diagnostics formerly Boehringer Mannheim, Indianapolis, Ind.). Subcloning Efficiency DH5α™ Competent Cells (Gibco/BRL) were transformed with the ligation mixture and cells were plated on LB media containing 75 ug/ml ampicillin. Plates were incubated overnight at 37 C. Individual colonies were selected for DNA extraction and DNA sequencing as described. Those plasmids which contained the ADF promoter fragment replacing the CaMV promoter were named pDAB621.

| Features of pDAB 621 | |
|---|---|
| bp of pDAB 621 | Description of feature |
| 1–2912 | correspond to bp 1–2912 of pDAB 305 (SEQ ID NO: 2) |
| 2913–3056 | reverse compliment of untranslated leader sequence (bp 735–878 of SEQ ID NO: 1) |
| 3057–3790 | reverse compliment of ADF promoter (bp 1–734 of SEQ ID NO: 1) and |
| 3791–6030 | correspond to 3557–5796 of pDAB 305 (SEQ ID NO: 2) |

EXAMPLE 4

Construction of pDAB625

Plasmid pDAB625 differs from plasmid pDAB620 essentially in that the ADF intron 1 is cloned immediately 3' to the ADF promoter. For creating the ADF promoter/ADF intron vector, the promoter and intron sequences were fused using a PCR splice overlap extension strategy (PCR Protocols: A Guide to Methods and Applications, ed. Innis, M.; Gelfand, D.; Sninsky, J.; White, T., 1990, Academic Press). The ADF promoter and ADF intron were amplified in separate reactions using suitable primers. Reaction conditions were as follows: 10 ng template DNA (SEQ ID NO:1 cloned into PCR® 2.1-Topo vector), 10 ul GeneAmp® 10×PCR buffer (PE/ABI), 100 pmoles each primer, 5 units AmpliTaq Gold™ Polymerase (PE/ABI) in a volume of 100 ul. Cycling was done in a GeneAmp® PCR System 9600 thermocycler programmed with the following profile: 95° C. 10 minutes, (94° C. 30 sec, 60° C. 30 sec, 72° C. 1 min) for 15 cycles, 72° C. for 5 minutes. The promoter fragment and the intron product were fused in a PCR reaction which contained the following components: 50 ng each PCR product, 30 ul 3.3×XL buffer (PE/ABI), 4 ul 25 mM magnesium acetate, 10 ul 2 mM dNTPs, 100 pmoles each primer, 6 units rTth DNA Polymerase (PE/ABI) in a final volume of 50 ul. Reactions were performed in a RoboCycler® Gradient 96 Temperature Cycler (Stratagene) using the following cycling profile: 940 C 1 minute, [94° C. 30 sec, 70° C. 4 minutes]×20 cycles, 72° C. 10 minutes. The resulting 2184 bp PCR product was run on a preparative agarose gel (EMC). The fragment was cut out and DNA was extracted using using GenElute Agarose Spin Columns (Supelco, Inc.). The 2184 bp fragment was bulked up in another PCR reaction, and the product of this reaction was cloned into PCR® 2.1-Topo (Invitrogen). Individual colonies were selected for DNA extraction and sequencing as described above. For cloning the ADF promoter/ADF intron fusion into pDAB305, the fusion product was isolated from the recombinant PCR® 2.1-Topo (Invitrogen) clones as a HindIII and NcoI fragment by digestion with HindIII and NcoI restriction enzymes (New England Biolabs Inc.). Plasmid pDAB305 was prepared by digestion with HindIII and NcoI (NEB) to drop out the existing promoter and intron/leader. The ADF promoter/ADF intron HindIII/NcoI promoter fragment was combined with the HindIII/NcoI deleted pDAB305 and ligated using the Rapid DNA Ligation Kit (Roche Diagnostics formerly Boehringer Mannheim, Indianapolis, Ind.). Subcloning Efficiency DH5α™ Competent Cells (Gibco/BRL) were transformed with the ligation mixture, and cells were plated on LB media containing 75 ug/ml ampicillin. Plates were incubated overnight at 37° C. Individual colonies were selected for DNA extraction and DNA sequencing as described. Those plasmids which contained the ADF promoter/ADF intron fragment replacing the CaMV promoter/ADH intron were named pDAB625.

| Features of pDAB 625 | |
|---|---|
| bp of pDAB 625 | Description of feature |
| 1–2538 | correspond to bp 1–2538 of pDAB 305 (SEQ ID NO: 2) |
| 2539–3818 | reverse compliment of ADF intron (bp 882–2161 of SEQ ID NO: 1) |
| 3819–3962 | reverse compliment of ADF leader sequence (bp 735–878 of SEQ ID NO: 1) |
| 3963–4694 | reverse compliment of ADF promoter (bp 1–734 of SEQ ID NO: 1) except for the following modifications resulting from the PCR procedure: G deleted between bp 4059 and 4060, G deleted between bp 4131 and 4132, A substituted for G at 4195, and G substituted for A at 4508. |
| 4695–6934 | correspond to 3557–5796 of pDAB 305 (SEQ ID NO: 2) |

EXAMPLE 5

Transient Testing of ADF-GUS Constructs

Type II callus cultures were initiated from immature zygotic embryos of the genotype "Hi-II" (Armstrong et al. (1991) Maize Genet. Coop. News Lett. 65:92–93). Embryos were isolated from greenhouse-grown ears from crosses between Hi-II parent A and Hi-II parent B or $F_2$ embryos derived from a self- or sib-pollination of a Hi-II plant. Immature embryos (1.5 to 3.5 mm) were cultured on 15Ag10 callus initiation medium consisting of N6 salts and vitamins (Chu et al, (1978) *The N6 medium and its application to anther culture of cereal crops.* Proc. Symp. Plant Tissue Culture, Peking Press, 43–56), 1.0 mg/L 2,4-D, 25 mM L-proline, 100 mg/L casein hydrolysate, 10 mg/L $AgNO_3$, 2.5 g/L GELRITE (Schweizerhall, South Plainfield, N.J.), and 20 g/L sucrose, with a pH of 5.8. After four to six weeks callus was subcultured onto maintenance medium (initiation medium in which $AgNO_3$ was omitted and L-proline was reduced to 6 mM). Selection for Type II callus took place for ca. 12–16 weeks.

Each of the test GUS constructs was co-precipitated onto gold particles with pDeLux (containing a 35S modified promoter driving luciferase with the Nos 3' UTR) according to the following protocol. Equal molar amounts of the GUS plasmids were used. A total of 70 μg of DNA, 35 μg of pDeLux plus 35 μg of test DNA and Bluescript™ DNA (Stratagene, La Jolla, Calif.) when necessary, was diluted in sterile water to a volume of 150 μL. The DNA and water were added to 30 mg of surface-sterilized 1.0 μM spherical gold particles (Bio-Rad Laboratories, Hercules, Calif.). The mixture was vortexed briefly (approximately 15 seconds) before adding 37 μL of 2.5 M calcium chloride and 15 μL of 0.1 M spermidine (free base). After vortexing for 30 seconds, the DNA and gold were allowed to precipitate from solution. The supernatant was removed and 1 mL of ethanol was added. The DNA/gold mixture was diluted 1:4 before use for transformation.

Type II callus was pretreated on osmotic medium for approximately 16 hours. Osmotic medium consisted of maintenance medium with 0.2 M sorbitol and 0.2 M mannitol. Afterward, the callus was placed onto 60×20 mm plates of osmotic medium solidified with 2% agar for helium blasting. Cages of 104 μm mesh screen covered each target (500–600 mg of callus) to prevent splattering and loss of tissue. Targets were individually blasted with DNA/gold mixture using the Dow AgroSciences Helium Blast Device 1.0 (U.S. Pat. No. 5,141,131). Under a partial vacuum of 25 inches of Hg, at a shooting distance of 10 cm and pressure of 1500 psi, DNA/gold mixture was accelerated toward each target four times, delivering 20 μL per shot. The targets were rotated 180° after each blast. The tissue was also mixed halfway through the procedure to expose unblasted callus. Upon completion of blasting, the targets were placed onto the original osmotic medium for overnight incubation at 26° C. in the dark.

Four Type II callus cell lines were selected for each experiment. Two targets from each line were used per construct. Also, two nontransformed controls (NTC) composed of tissue pooled from all four lines were included. The controls were transferred to osmotic and blasting media according to the protocol above, but were not subjected to helium blasting.

Approximately 20 hours after blasting, 200–400 mg of each target was transferred to a 1.5 mL sample tube (Kontes, Vineland, N.J.). For extraction of proteins, callus was homogenized using a stainless steel Kontes Pellet Pestle powered by a 0.35 amp, 40 Watt motor (Model 102, Rae Corporation, McHenry, Ill.) at a setting of "90". Cell Culture Lysis Reagent from a Luciferase Assay kit (Promega, Madison, Wis.) served as the extraction buffer. Protease inhibitors, phenylmethylsulfonyl fluoride (PMSF) and leupeptin hemisulfate salt, were added to the lysis buffer at the concentrations of 1 M and 50 μM, respectively. Before grinding, 0.5 μL of lysis buffer per mg tissue was added to the sample tube. The callus was homogenized in four 25-second intervals with a 10-second incubation on ice following each period of grinding. Afterward, 1.0 μL of lysis buffer per mg tissue was added to the sample which was placed on ice until all sample grinding was completed. The samples were then centrifuged twice at 5° C. for 7 minutes at full speed (Eppendorf Centrifuge Model 5415). After the first spin, the supernatant from each tube was removed and the pellet was discarded. Callus extracts (supernatants) were also collected after the second spin and maintained on ice for GUS and LUC analyses.

From the LUC Assay kit, LUC Assay Buffer was prepared according to the manufacturer's instructions. This buffer was warmed to room temperature and loaded into the dispensing pump of an automatic luminescence photometer (Model 1251 Luminometer and Model 1291 Dispenser, Bio-Orbit, Finland). Each sample was tested in triplicate by adding 20 μL of extract to three polypropylene luminometer vials (Wallac, Gaithersburg, Md.). Per vial, 100 μL of assay buffer was dispensed and luminescence was detected over a 45-second integration period. "Blank reactions", including 20 μL of extraction buffer rather than callus extract, were also measured within each experiment.

For analysis of GUS activity, a GUS-Light™ assay kit (Tropix, Bedford, Mass.) was used. Again, each sample was tested in triplicate, using 20 μL of extract per luminometer vial. GUS-Light™ Reaction Buffer was prepared from the assay kit according to the manufacturer's instructions. This buffer was warmed to room temperature and added in 180 μL aliquots to each luminometer vial at 10-second intervals. After a one hour incubation at room temperature, 300 μL of GUS-Light™ Light Emission Accelerator Buffer was added and luminescence was detected over a 5-second integration period. "Blank reactions" were also included in the GUS assay, using 20 μL of extraction buffer rather than callus extract.

GUS and LUC results were reported in relative light units (RLU). Both "blank" and NTC readings were subtracted from sample RLU levels. For comparison of one GUS construct to another, GUS readings were normalized to LUC data using the square roots of each to calculate a GUS/LUC ratio for every sample tested. The ratios for all samples per construct were then averaged and the means were compared using a T-test for analysis of statistical significance. A modified 35S promoter (35T)/GUS/Nos poly A construct (pDAB305) was used as a control in each experiment. Test construct expression levels were reported as a percent of pDAB305 activity.

Plasmid pDAB620 demonstrated no expression above background, relative to the 35T control. However, in repeated experiments pDAB621 and pDAB625 averaged 62% and 82% of the standard, respectively. pDAB621 consistently expressed at levels significantly lower than the control. Whereas, pDAB625 resulted in expression which was somewhat more variable and in some cases proved to be as good as pDAB305.

EXAMPLE 6

Stable Expression in Maize

ADF promoter activity was characterized by the frequency of callus formation of maize tissue transformed with plasmid pDAB630 (ADF promoter/ADF intron/PAT/nosA) in the presence of media containing a selective agent. Transgenic maize events containing PAT under control of the rice actin promoter were also produced to serve as internal controls. In a total of 15 side-by-side experiments, the ADF construct either performed as-well-as or outperformed the rice actin promoter construct with respect to the recovery of herbicide resistant isolates. Southern analysis confirmed the presence of the PAT gene in all ADF events produced.

EXAMPLE 7

Transgenic Maize

Transgenic plants from two events transformed with plasmid pDAB625 were analyzed for GUS expression in leaf tissue. In quantitative assays, GUS levels equivalent to 0.02% total extractable protein were observed.

The invention claimed is:

1. An construct comprising base pairs 1–734 of SEQ ID NO:1 operably linked to a heterologous nucleic acid molecule.

2. An expression vector comprising the construct of claim 1.

3. A transformed plant comprising at least one plant cell that contains the construct of claim 1.

4. Seed or grain that comprises the construct of claim 1.

* * * * *